(12) United States Patent
Bjork et al.

(10) Patent No.: US 9,480,472 B2
(45) Date of Patent: *Nov. 1, 2016

(54) MINIMALLY INVASIVE PORTAL SYSTEM

(71) Applicant: Spineology Inc., St. Paul, MN (US)

(72) Inventors: Todd Bjork, River Falls, WI (US); Dan McPhillips, Ham Lake, MN (US)

(73) Assignee: Spineology Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/827,990

(22) Filed: Aug. 17, 2015

(65) Prior Publication Data
US 2015/0351733 A1    Dec. 10, 2015

Related U.S. Application Data

(63) Continuation of application No. 13/544,715, filed on Jul. 9, 2012, now Pat. No. 9,107,650.

(60) Provisional application No. 61/506,024, filed on Jul. 8, 2011.

(51) Int. Cl.
| | |
|---|---|
| *A61B 17/00* | (2006.01) |
| *A61B 19/00* | (2006.01) |
| *A61B 17/02* | (2006.01) |
| *A61B 17/34* | (2006.01) |
| *A61B 17/29* | (2006.01) |

(52) U.S. Cl.
CPC ......... *A61B 17/025* (2013.01); *A61B 17/3421* (2013.01); *A61B 90/50* (2016.02); *A61B 2017/0256* (2013.01); *A61B 2017/2927* (2013.01); *A61B 2090/309* (2016.02)

(58) Field of Classification Search
CPC ................ A61B 17/04; A61B 17/025; A61B 2017/0256; A61B 17/3415; A61B 17/3421; A61B 17/3423

USPC .................................. 600/104, 114
See application file for complete search history.

(56) References Cited

U.S. PATENT DOCUMENTS

| | | | | |
|---|---|---|---|---|
| 5,354,314 | A * | 10/1994 | Hardy ..................... | A61B 19/20 378/206 |
| 5,402,801 | A * | 4/1995 | Taylor ................. | A61B 19/5244 128/898 |
| 5,562,696 | A * | 10/1996 | Nobles .................... | A61B 1/042 600/101 |
| 5,569,205 | A * | 10/1996 | Hart .................... | A61B 17/3462 604/167.03 |
| 6,152,871 | A * | 11/2000 | Foley .................. | A61B 17/3421 600/102 |
| 6,799,074 | B1 * | 9/2004 | Thomas ............... | A61B 19/201 606/130 |
| 7,198,598 | B2 * | 4/2007 | Smith ................ | A61B 17/3421 600/102 |
| 7,833,231 | B2 * | 11/2010 | Skakoon .............. | A61B 19/201 606/130 |
| 8,795,167 | B2 * | 8/2014 | Ainsworth ......... | A61B 17/0642 600/222 |
| 9,107,650 | B2 * | 8/2015 | Bjork .................... | A61B 17/025 |

(Continued)

*Primary Examiner* — Ahmed Farah
(74) *Attorney, Agent, or Firm* — Skaar Ulbrich Macari, P.A.

(57) ABSTRACT

A minimally invasive surgical portal system, kit, device and method may include a top ring assembly removably connected to an arm of a table mounted frame to provide stability and a secure trajectory. The portal system may include a top-ring assembly which may mount to an arm of a table mounted frame. The system may include a removable connection mechanism comprising a spring loaded collar configured to removably connect the top ring assembly to a table mounted frame. A variable adjustment positioner may be removably connected to the arm of the table mounted frame. The system may also include a depth positioning mechanism. The system may further include a light source configured to be placed down the portal tube.

12 Claims, 1 Drawing Sheet

(56) References Cited

U.S. PATENT DOCUMENTS

| | | | |
|---|---|---|---|
| 2006/0206009 A1* | 9/2006 | Von Wald | A61B 17/02 600/231 |
| 2006/0235389 A1* | 10/2006 | Albert | A61B 17/7032 128/898 |
| 2007/0055291 A1* | 3/2007 | Birkmeyer | A61B 90/13 606/130 |
| 2009/0000627 A1* | 1/2009 | Quaid | A61B 17/1764 128/898 |
| 2009/0036746 A1* | 2/2009 | Blackwell | A61B 17/0206 600/219 |

* cited by examiner

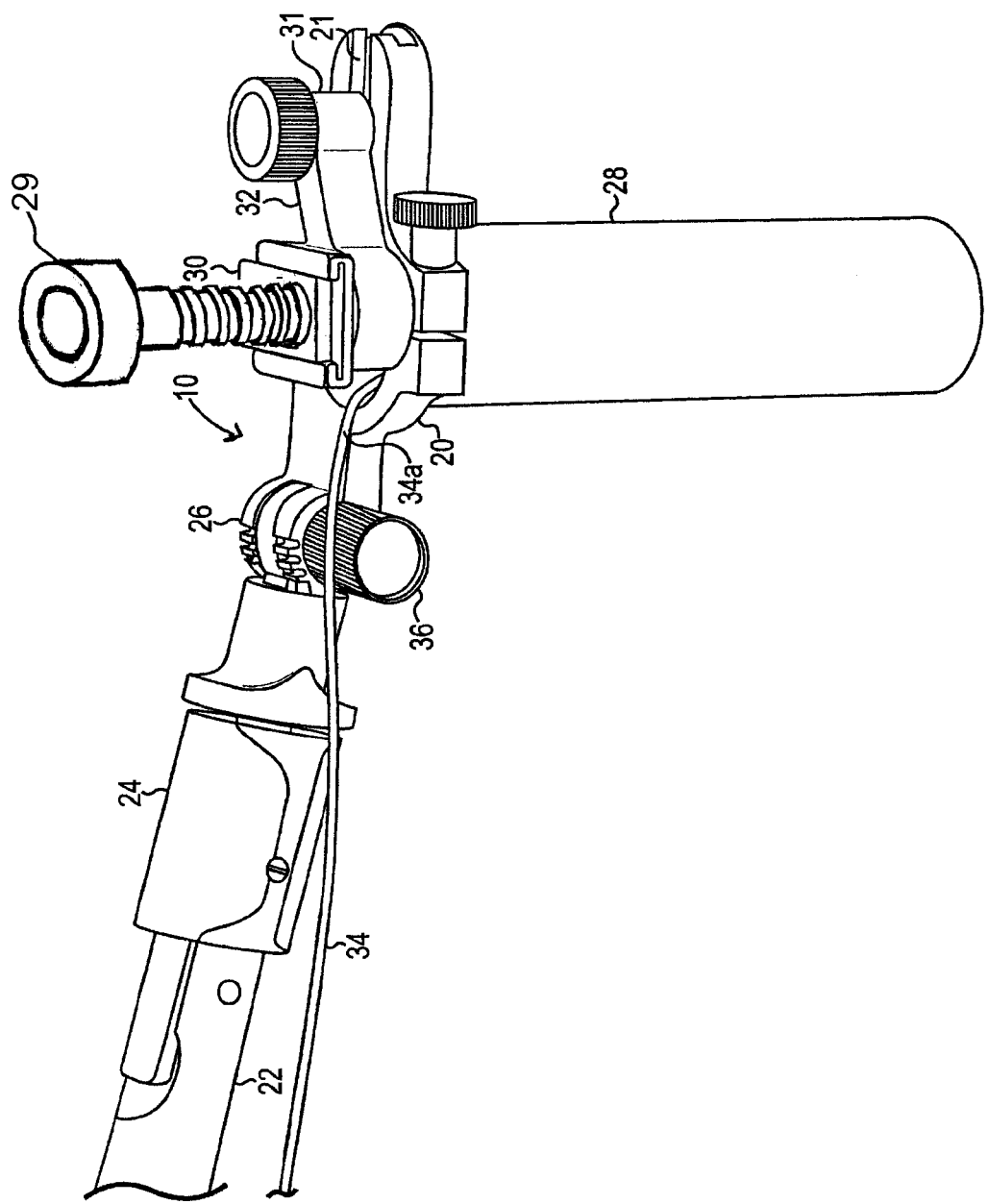

MINIMALLY INVASIVE PORTAL SYSTEM

PRIORITY

This application is a continuation of U.S. patent application Ser. No. 13/544,715, filed Jul. 9, 2012, which claims the priority benefit of U.S. Provisional Application No. 61/506,024, filed on Jul. 8, 2011, both of which are hereby incorporated by reference herein in their entirety.

FIELD

The present invention relates generally to a minimally invasive surgical ("MIS") portal system. More particularly the present invention relates to an adjustable MIS surgical portal system.

BACKGROUND

MIS techniques have become increasingly popular due to the rapid healing and greater efficiency provided by such techniques. As these techniques have been developed, workers and surgeons have been faced with the problem of access to the surgical site. Various tools have been designed to address with this problem, however there remains a need to provide for an MIS surgical portal system with enhanced functionality.

SUMMARY

The various embodiments of the disclosed MIS surgical portal system, apparatus and method provides for enhanced functionality and ease of use in MIS techniques and procedures. The MIS surgical portal may be removably connected to a table mounted frame to provide stability and a secure trajectory. In one embodiment, the portal system may include a top-ring assembly which may mount to an arm of a table mounted frame. Other suitable mounting assemblies may be used.

According to another embodiment of the present invention, the system may include a removable connection mechanism comprising a spring loaded collar configured to removably connect the top ring assembly to a table mounted frame. Such a collar may rotate to lock and unlock the connection to the table mounted frame. In another embodiment of the present invention, the system may include a removable connection mechanism comprising a ball and socket mechanism configured to removably connect the top ring assembly to a table mounted frame.

In an embodiment of the present invention, a variable adjustment positioner may be removably connected to the arm of the table mounted frame. In one embodiment of the present invention, the variable adjustment positioner may be part of the removable connection mechanism. According to one aspect of the present invention, the portal system allows a retractor tube and working cannula to be placed at any desired vertebral level. According to an embodiment of the present invention, the system is adjustable such that multiple vertebral levels may be accessed without removing the system.

In one embodiment of the present invention, the system may include a depth positioning mechanism, for example, but not limited to, the method and device disclosed in U.S. Patent Application Publication No. 2010/0331882 A1, the entirety of which is hereby incorporated by reference herein.

According to an embodiment of the present invention, the depth positioning mechanism may support and dissipate impact forces.

In one aspect of the present invention, the working cannula may be positioned on the top ring assembly using a connector. In an embodiment of the present invention, the connector may be curved to provide more visibility and greater working area. In another embodiment of the present invention, the connector may be straight. According to one aspect of the present invention, the connector may allow the user to position and reposition the working cannula as desired and then lock the working cannula in place providing support and guidance for instrument placement.

In yet another embodiment the working cannula may be positioned on the top ring assembly using a clamp, thumb screw or any other suitable mechanism. In another embodiment the working cannula may be positioned on the top ring assembly with an eccentric locking mechanism.

In one embodiment of the present invention, a light source is configured to be placed down the portal tube. In one embodiment of the present invention, the light source may be held tight to the portal tube using an adjustable mechanism, for example, but not limited to a knob or any other suitable mechanism. In an embodiment the light source may be a disposable single use fiber optic cable. According to an embodiment of the present invention, the light source may be pre-bent to a desired fit. In one embodiment, the light source may be a low intensity LED.

The detailed technology and preferred embodiments implemented for the subject invention are described in the following paragraphs accompanying the appended drawings for people skilled in this field to well appreciate the features of the claimed invention. It is understood that the features mentioned hereinbefore and those to be commented on hereinafter may be used not only in the specified combinations, but also in other combinations or in isolation, without departing from the scope of the present invention.

BRIEF DESCRIPTION OF THE DRAWINGS

FIG. 1 depicts a side perspective view of an embodiment of the present invention.

While the invention is amenable to various modifications and alternative forms, specifics thereof have been shown by way of example in the drawings and will be described in detail. It should be understood, however, that the intention is not to limit the invention to the particular example embodiments described. On the contrary, the invention is to cover all modifications, equivalents, and alternatives falling within the spirit and scope of the invention as defined by the appended claims. For illustrative purposes, cross-hatching, dashing or shading in the figures is provided to demonstrate sealed portions and/or integrated regions or devices for the package.

DETAILED DESCRIPTION

In the following descriptions, the present invention will be explained with reference to example embodiments thereof. However, these embodiments are not intended to limit the present invention to any specific example, embodiment, environment, applications or particular implementations described in these embodiments. Therefore, description of these embodiments is only for purpose of illustration rather than to limit the present invention. It should be appreciated that, in the following embodiments and the attached drawings, elements unrelated to the present invention are omitted from depiction; and dimensional relationships among individual elements in the attached drawings are illustrated only for ease of understanding, but not to limit the actual scale.

As can be seen in FIG. 1, the MIS portal system 10 of the present invention may include a top ring assembly 20 removably connected to an arm 22 of a table mounted frame. A removable connection mechanism 24 may be used to removably connect assembly 20 to arm 22. In one embodiment, removable connection mechanism 24 may be a spring loaded collar, as shown in FIG. 1. In another embodiment of the present invention, a ball and socket or other suitable connection mechanism may be used to removably connect assembly 20 to arm 22.

In one embodiment, variable positioner 26 adjusts the trajectory of system 10 such that multiple vertebral levels may be accessed without removing system 10 from arm 22. In one embodiment, variable positioner 26, may be removably connected to arm 22. In one embodiment of the present invention, variable positioner 26 may be part of removable connection mechanism 24. In another embodiment, variable positioner 26 may be separate from removable connection mechanism 24. According to one aspect of the present invention, the portal system allows a retractor tube 28 and working cannula 29 to be placed at any desired vertebral level.

In one embodiment working cannula 29 may be seated into depth positioning mechanism 30, for example, but not limited to, as described in the method and device disclosed in U.S. Patent Application Publication No. 2010/0331882 A1. Depth adjustment mechanism 30 may be adjustably secured to assembly 20 using a connector 32. According to one aspect, connector 32 may be placed in channel 21 of assembly 20 such that connector 32 may slide along channel 21 allowing for adjustable placement of cannula. Further, connector 32 may swivel about its connection 31 to provide 360 degrees of adjustability of the working cannula 29 within retractor tube 28.

In an embodiment of the present invention, connector 32 may be curved to provide more visibility and greater working area. In another embodiment of the present invention, connector 32 may be straight. According to one aspect of the present invention, connector 32 may releasably lock the working cannula 29 in place providing support and guidance for instrument placement while permitting the user to adjust placement of working cannula 29 as desired.

In one embodiment of the present invention, light source 34 is configured to be placed down retractor tube 28. In one embodiment of the present invention, light source 34 may be held tight to retractor tube 28 using an adjustable mechanism 36, for example, but not limited to a knob or any other suitable mechanism. In an embodiment light source 34 may be a disposable single use fiber optic cable. According to an embodiment of the present invention, light source 34 may be pre-bent 34a to a desired fit. In one embodiment, the light source may be a low intensity LED.

The present invention may be embodied in other specific forms without departing from the spirit or essential attributes thereof, and it is, therefore, desired that the present embodiment be considered in all respects as illustrative and not restrictive. Those skilled in the art may recognize other equivalents to the specific embodiment described herein which equivalents are intended to be encompassed by the claims attached hereto.

What is claimed is:

1. A minimally invasive spinal surgical portal system, comprising:
   a top ring assembly removably connected to a table mounted frame and extending distally from the table;
   a variable positioner configured to adjust the trajectory of the system such that multiple levels of a spine may be accessed without removing the system from the frame;
   a retractor tube movably connected to the assembly;
   a working cannula; and
   a connector operatively connected to the working cannula, the connector being rotatably connected to the assembly such that the working cannula is swivelable about a vertical axis with respect to the retractor tube.

2. The system of claim 1, wherein the connector is configured to linearly slide along a channel defined in the assembly to provide translating motion to the working cannula with respect to the retractor tube.

3. The system of claim 1, wherein the connector is curved.

4. The system of claim 1, wherein the variable positioner is configured to rotate the system about a horizontal axis that is perpendicular to the distal extending direction of the top ring assembly.

5. The system of claim 1, wherein the connector releasably locks the working cannula into place.

6. The system of claim 1, further including a light source positioned in the retractor tube.

7. A method of performing minimally invasive spinal surgery using a portal system, the method comprising:
   positioning a retractor tube;
   securing a top ring assembly to a table mounted frame that extends in a distal direction;
   movably connecting a connector to the top ring assembly;
   swiveling the connector about a vertical axis with respect to the retractor tube;
   creating an access path to a surgical site; and
   placing a working cannula into the surgical site.

8. The method of claim 7, further comprising rotating a trajectory of the retractor tube about a horizontal axis that is perpendicular to the distally extending direction.

9. The method of claim 7, further comprising linearly sliding the connector along a channel defined in the table mounted frame to provide translating motion to the working cannula with respect to the retractor tube.

10. A method of performing minimally invasive spinal surgery using a portal system, the method comprising:
    positioning a retractor tube;
    securing a top ring assembly to a table mounted frame that extends in a distal direction;
    movably connecting a connector to the top ring assembly;
    rotating a trajectory of the retractor tube about a horizontal axis that is perpendicular to the distally extending direction;
    creating an access path to a surgical site; and
    placing a working cannula into the surgical site.

11. The method of claim 10, further comprising swiveling the connector about a vertical axis with respect to the retractor tube.

12. The method of claim 10, further comprising linearly sliding the connector along a channel defined in the table mounted frame to provide translating motion to the working cannula with respect to the retractor tube.

* * * * *